United States Patent [19]
Lewis et al.

[11] Patent Number: 5,314,416
[45] Date of Patent: May 24, 1994

[54] LOW FRICTION SYRING ASSEMBLY

[75] Inventors: Anthony K. Lewis, St. Charles; Eugene E. Weilbacher, Ellisville, both of Mo.

[73] Assignee: Sherwood Medical Company, St. Louis, Mo.

[21] Appl. No.: 902,184

[22] Filed: Jun. 22, 1992

[51] Int. Cl.⁵ .......................................... A61M 5/315
[52] U.S. Cl. ..................................... 604/219; 128/763
[58] Field of Search ........................... 128/760–764; 604/218, 219, 222, 230, 110, 228

[56] References Cited

U.S. PATENT DOCUMENTS

| | | | |
|---|---|---|---|
| D. 248,873 | 8/1978 | Raitto | D24/130 |
| D. 254,446 | 3/1980 | Raitto | D24/130 |
| 1,737,844 | 12/1929 | Heineman et al. | |
| 2,607,342 | 8/1952 | Abel | |
| 2,856,923 | 10/1958 | Roger et al. | |
| 2,882,899 | 4/1959 | Nogier et al. | |
| 2,886,034 | 5/1959 | Robinson et al. | |
| 2,895,773 | 7/1959 | McConnaughey | |
| 2,907,330 | 10/1959 | Laub | |
| 3,026,872 | 3/1962 | Prater, Jr. | |
| 3,028,862 | 4/1962 | Prater, Jr. | |
| 3,059,639 | 10/1962 | Blackman et al. | |
| 3,135,260 | 6/1964 | Hamilton | |
| 3,147,753 | 9/1964 | Nogier et al. | |
| 3,150,801 | 9/1964 | Hamilton | 222/158 |
| 3,253,592 | 5/1966 | Pechmann | |
| 3,281,023 | 10/1966 | Bruck et al. | 222/390 |
| 3,366,103 | 1/1968 | Keller | 128/2 |
| 3,581,956 | 6/1971 | Reid | 222/386 |
| 3,890,956 | 6/1975 | Moorehead | 128/765 |
| 4,030,496 | 6/1977 | Stait et al. | 604/222 |
| 4,057,052 | 11/1977 | Kaufman et al. | 128/765 |
| 4,074,715 | 2/1978 | Geiger | 604/230 |
| 4,159,713 | 7/1979 | Prais | 128/765 |
| 4,178,941 | 12/1979 | Raitto | 128/763 |
| 4,212,307 | 7/1980 | Raitto | 128/763 |
| 4,212,309 | 7/1980 | Moorehead | 128/766 |
| 4,215,701 | 8/1980 | Raitto | 128/763 |
| 4,245,654 | 1/1981 | Raitto | 128/765 |
| 4,266,557 | 5/1981 | Merry | 128/763 |
| 4,267,846 | 5/1981 | Kontos | 128/765 |
| 4,299,238 | 11/1981 | Baidwan et al. | 128/763 |
| 4,303,070 | 12/1981 | Ichikawa et al. | 604/222 |
| 4,320,770 | 3/1982 | Etherington et al. | 128/766 |
| 4,327,745 | 5/1982 | Ford, Jr. | 128/765 |
| 4,340,067 | 7/1982 | Rattenborg | 128/763 |
| 4,354,507 | 10/1982 | Baitto | 128/763 |
| 4,363,329 | 12/1982 | Raitto | 128/765 |
| 4,372,325 | 2/1983 | Raitto | 128/763 |
| 4,373,535 | 2/1983 | Martell | 128/765 |
| 4,411,725 | 10/1983 | Raitto | 156/353 |
| 4,421,123 | 12/1983 | Percarpio | 128/766 |
| 4,448,206 | 5/1984 | Martell | 128/765 |
| 4,459,997 | 7/1984 | Sarstedt | 128/764 |
| 4,466,446 | 8/1984 | Baidwan et al. | 128/765 |
| 4,493,703 | 1/1985 | Butterfield | 604/110 |
| 4,500,310 | 2/1985 | Christinger | 604/228 |
| 4,519,402 | 5/1985 | Andersen | 128/765 |
| 4,543,093 | 9/1985 | Christinger | 604/228 |
| 4,572,210 | 2/1986 | McKinnon | 128/765 |
| 4,595,021 | 6/1986 | Shimizu et al. | 128/765 |
| 4,632,672 | 12/1986 | Kvitrud | 604/222 |
| 4,657,028 | 4/1987 | Rich et al. | 128/765 |
| 4,687,000 | 8/1987 | Eisenhardt et al. | 128/760 |
| 4,690,154 | 9/1987 | Woodford et al. | 128/765 |
| 4,703,763 | 11/1987 | McAlister et al. | 128/765 |
| 4,704,105 | 11/1987 | Adorjan et al. | 604/222 |
| 4,767,414 | 8/1988 | Williams et al. | 604/230 |
| 4,774,963 | 10/1988 | Ichikawa et al. | 128/763 |
| 4,820,278 | 4/1989 | Balisky | 604/218 |
| 4,821,738 | 4/1989 | Iwasaki et al. | 128/765 |

Primary Examiner—C. Fred Rosenbaum
Assistant Examiner—V. Alexander
Attorney, Agent, or Firm—Andrew J. Beck; Montgomery W. Smith; Richard D. Allison

[57] ABSTRACT

A syringe assembly including a plunger rod and a plunger tip which are designed to provide a low frictional resistance against the interior surface of the syringe barrel while the plunger rod is at rest but which will increase the sealing pressure between the plunger tip and the interior surface of the syringe barrel in proportion to the amount of force applied to the plunger rod. Additionally, the plunger rod may be moved in the syringe barrel in a laterally offset manner with respect to the longitudinal axis of the syringe barrel without significantly affecting the seal between the plunger tip and the syringe barrel.

22 Claims, 4 Drawing Sheets

LOW FRICTION SYRING ASSEMBLY

FIELD OF THE INVENTION

The present invention relates to a syringe assembly or other medical device wherein it is desirable to move a fluid through a conduit and more particularly to a plunger tip for use in a medical device which varies the amount of sealing pressure applied to the inner wall of a syringe barrel.

BACKGROUND OF THE INVENTION

A conventional syringe consists of a cylindrical barrel member, most commonly made of a thermoplastic material such as polypropylene. The conventional syringe typically has a reduced diameter distal end adapted to receive a needle thereon and an open proximal end adapted to receive a plunger rod assembly therein. The plunger rod assembly generally consists of an elongate plunger rod which is commonly made of a thermoplastic material such as polypropylene and a flexible plunger tip on the distal end thereof. The plunger tip is commonly made of an elastomeric material such as butyl or ethylene polypropylene rubber.

One of the functions of the plunger tip is to provide a substantially air tight seal with the interior surface of the syringe barrel so that movement of the plunger tip distally and proximally in the syringe barrel will cause medication, blood or other fluids to be drawn into or forced out of the distal end of the syringe barrel. The plunger tip is moved through the inside of the syringe barrel by applying axial force to the rigid plunger rod which has sufficient length to be accessible through the proximal end of the syringe barrel. Therefore, the preferred plunger tip is designed to have sufficient flexibility so that it will create a seal with the interior surface of the syringe barrel without creating excessive resistance to the movement of the plunger tip through the syringe barrel.

In order to ensure an air tight seal with the interior surface of the syringe barrel, plunger tips are typically manufactured with an outside diameter which is significantly larger than the inside diameter of the syringe barrel. The plunger tip is designed such that when the plunger tip is introduced into the syringe barrel, the plunger tip is compressed sufficiently to provide adequate pressure between the barrel and the plunger tip to seal this interface. As a result of the plunger tip design, the interface of the plunger tip and the barrel maintains, at all times, a sealing pressure sufficient to withstand the challenges of filling and injecting even though the same magnitude of sealing pressure may not be required when the syringe is not in use. A major drawback to this approach is that the increased diameter of the plunger tip increases the frictional resistance to movement of the plunger tip in the barrel.

U.S. Pat. Nos. 4,500,310 and 4,543,093 granted to Christinger disclose a variable sealing pressure plunger rod assembly which utilizes a thermoplastic plunger tip. As disclosed in these patents, the distal end of the plunger rod is modified to include one or more tapered surfaces thereon which are adapted to contact one or more similarly tapered surfaces on the interior surface of a thermoplastic plunger tip. When the plunger rod of the disclosed devices is moved distally in the barrel, the tapered distal surface of the plunger rod contacts the tapered distal surface on the interior surface of the plunger tip to create a force component which is directed substantially outwardly from the interface of the respective surfaces. As a result of the force component created by the contact between the respective tapered surfaces, the radial diameter of the plunger tip adjacent to a rib on the outer surface of the plunger tip, temporarily increases to increase the sealing pressure between the plunger tip and the interior surface of the barrel. These patents disclose further embodiments wherein the plunger rod and thermoplastic plunger tip have similarly tapered proximal surfaces such that the outer diameter of the plunger tip adjacent to a proximal rib is temporarily increased as the plunger rod assembly is withdrawn proximally in the syringe barrel.

One of the potential problems with the designs disclosed in the Christinger patents is that the tolerances between the dimensions of the interior of the plunger tip and distal end of the plunger rod are very important to the efficient operation of the disclosed syringe. The critical dimensions required for proper operation of these syringes may be difficult to maintain with the quantity of syringes that are typically produced by a manufacturer. If these critical dimensions are not maintained, the tapered surfaces of the plunger rod and plunger rod may not be properly aligned when the syringe is assembled. If the tapered surfaces are not properly aligned, the plunger tip may pull off the distal end of the plunger rod during aspiration of the syringe or the desired expansion of the plunger tip may not be achieved, thereby creating the possibility that a proper seal will not be formed between the plunger tip and the syringe barrel. Finally, it is also possible that the distal end of the plunger rod may become wedged within the interior of the plunger tip so that the radial expansion of the plunger tip is maintained when the plunger rod is moved in the opposite direction. If this were to occur, the frictional resistance to further movement of the plunger rod through the syringe barrel would be greatly increased.

A further potential problem with the designs disclosed in Christinger patents occurs when the plunger rod is canted slightly in the syringe barrel. If the user applies a pressure to the plunger rod which is not directed fully along the longitudinal axis of the syringe barrel, the expansion of the plunger tip along the interior surface of the syringe barrel may not be applied equally along the interior surface of the syringe barrel and the plunger tip may leak. This potential problem is further magnified if the tapered surfaces of the plunger rod and plunger tip are misaligned.

U.S. Pat. No. 2,895,773 granted to McConnaughey discloses a variable diameter tensed ring piston. As disclosed in this patent, a piston cap is stretched over a plunger head on a plunger rod such that the piston cap is longitudinally stretched between a pair of rings located on the external surface of the plunger cap. According to this patent, the longitudinal stretching of the plunger cap between the rings tends to bring the rings back towards their normal position in relation to each other, thereby providing a tighter and more positive seal when the plunger rod is in a static position than when the plunger rod is moved distally or proximally in the syringe barrel.

The present invention is intended to provide a plunger rod assembly and syringe which may be readily mass produced and which will expand the diameter of the distal or proximal portion of the plunger tip consistently and reliably upon the application of distally or proximally directed forces thereto by the plunger rod to provide an efficient seal between the plunger tip and the syringe barrel while minimizing the force necessary to move the plunger rod assembly through the syringe barrel.

SUMMARY OF THE INVENTION

The plunger rod assembly of the present invention is useful for drawing fluid into or pushing fluid out of a syringe barrel or receptacle. The syringe barrel or receptacle includes an inside wall and is provided with means for receiving the plunger rod assembly therein and a means for communication with the exterior of the syringe barrel or receptacle. The plunger rod assembly of the present invention preferably includes an elongate plunger rod and a flexible plunger tip. The preferred plunger rod includes a rigid elongate shaft portion with an enlarged circular finger member on the proximal end and also a circular portion with a tapered portion and a flat surface on the distal end thereof.

The preferred plunger tip is a flexible cylindrically-shaped member having an annular side wall with a front wall connected to the distal portion of the side wall and a partial rear wall connected to the proximal portion of the side wall. The exterior surface of the side wall is slightly smaller in diameter than the interior diameter of the syringe barrel or receptacle. Additionally, distal and proximal circumferential ribs extend radially outwardly from the distal and proximal portions of the side wall. The distal and proximal circumferential ribs have a diameter which is slightly greater than the interior diameter of the syringe barrel such that the ribs are slightly compressed against the interior surface of the syringe barrel when the plunger rod is at rest. The interior surface on the plunger tip includes an inside surface of the front wall and an a flexible lip member which extends inwardly and rearwardly from the interior surface of the side wall adjacent to the front wall. Additionally, a rear wall extends inwardly from the proximal portion of the side wall to form a reduced diameter opening at the proximal end of the plunger tip.

Another embodiment of the plunger rod assembly of the present invention consists of a modified plunger rod and a modified plunger tip for use in a receptacle or syringe barrel. In this embodiment, the distal end of the plunger rod preferably includes a bulbous or semicircularly-shaped contact member thereon. The contact member provides a variable distal force to the lip member on the interior surface of the plunger tip such that as the distal force of the plunger rod assembly is increased in the receptacle or syringe barrel, a corresponding increase in the radial outward expansion of the distal portion of the plunger tip will be created Yet another embodiment of the present invention consists of a modified plunger tip for use with either of the plunger rods described above.

The present invention increases the sealing pressure between the plunger tip and the interior surface of the syringe barrel by direct contact between the distal end of the plunger rod and the interior of the plunger tip and by flexing the front wall of the plunger tip in response to the changes in pressure in the distal end of the syringe barrel as described below.

In the present invention, the sealing pressure exerted by the distal rib member on the interior surface of the syringe barrel will vary according to magnitude of the force of the distally directed pressure applied to the plunger rod by the user. Therefore, if the user applies a large distally directed force against the plunger rod, the lip member in the interior of the plunger tip will flex in response to the large distally directed force applied by the plunger rod to the lip member. The flexing of the lip member is then translated into a radially outwardly directed force which causes the distal rib member to expand against the interior surface of the syringe barrel. If a smaller distally directed force is applied to the plunger rod by the user, a similarly reduced radially outwardly directed force will be applied to the distal rib member due to the relatively smaller amount of flexing of the lip member caused by the plunger rod.

A further aspect of the present invention relates to the front wall of the plunger tip and the side wall of the distal lip member. The thickness of the front wall is chosen to increase the effectiveness of the distal seal of the plunger tip such that when fluids are expelled from the syringe assembly, an increased pressure is created distally of the plunger tip in the distal end of the syringe assembly. With the present invention, the increased pressure on the front wall of the plunger tip causes the front wall of the plunger tip to compress inwardly This compression creates a further outwardly directed force which increases the radial expansion of the distal portion of the plunger tip thereby further increasing the effectiveness of the seal created between the distal rib member and the syringe barrel.

The front wall of the plunger tip is also designed to assist in sealing the proximal portion of the plunger tip when the plunger rod assembly is withdrawn from the syringe barrel. As the plunger rod assembly is withdrawn from the syringe barrel, a slight vacuum is created distally of the plunger tip in the distal end of the syringe barrel. When this occurs, the front wall of the plunger tip is designed to flex or stretch distally. This flexing of the front wall causes a small reduction in the outer diameter of the distal portion of the plunger tip and is believed to cause a slight canting of the side wall of the plunger tip along the distal end of the plunger rod which then slightly increases the radial expansion of the proximal portion of the plunger tip. Therefore, when the front wall of the plunger tip is flexed distally due to the reduced pressure distally of the plunger tip, the frictional contact between the distal portion of the plunger tip and the syringe barrel is reduced while the frictional contact between the proximal portion of the plunger tip and the syringe barrel is increased.

In the present invention, the rear wall of the plunger tip is sized to prevent the plunger tip from being pulled off the distal end of the plunger rod as the plunger rod assembly is withdrawn in the syringe barrel. Additionally, the interior surface of the rear wall is tapered rearwardly so that the perpendicularly oriented proximal surface on the plunger rod will contact the tapered portion of the wall thereby creating an outwardly directed force which causes the proximal portion of the plunger tip to expand radially outwardly against the interior surface of the syringe barrel as the plunger rod is moved proximally in the syringe barrel thereby forming the primary seal between the proximal rib member and the inner surface of the syringe barrel.

Therefore, the present invention provides a reduced sealing pressure between the proximal and distal rib members on the plunger tip and the interior surface of the syringe barrel when the plunger rod assembly is at rest in the syringe barrel. When the plunger rod assembly is moved distally in the syringe barrel to expel fluids from the syringe barrel, the radial circumference of the distal rib on the plunger tip is increased in proportion to the amount of distally directed pressure exerted by the plunger rod. When the plunger rod assembly is moved proximally in the syringe barrel to aspirate fluids into the syringe barrel, the radial circumference of the proximal rib on the plunger tip is similarly increased. Because the preferred form of the present invention relies on contact between a flat surface on the distal end of the plunger rod and the lip member on the interior surface of the plunger tip, the tolerances between the respective parts are not as critical as with prior devices and there is little likelihood that the plunger tip will be improperly wedged onto the distal end of the plunger rod. Additionally, due to the presence of the free space between the distal end of the plunger rod and the interior of the plunger tip, lateral forces may be applied to the proximal end of the plunger rod without breaking the seal formed between the respective rib members on the plunger tip and the interior surface of the syringe barrel.

BRIEF DESCRIPTION OF THE DRAWINGS

FIG. 5 is a partial cross-sectional view of an alternate embodiment of the present invention showing a modified plunger rod assembly in a cross-sectioned view of a syringe barrel;

DETAILED DESCRIPTION OF THE PREFERRED EMBODIMENTS

In the preferred embodiments described herein, the present invention is intended to be used with a conventional syringe; however, the plunger rod assembly and more particularly, the plunger tip of the present invention may be used in a number of devices wherein it is desirable to increase the sealing pressures of a device whenever a plunger tip or similar member is moved in a fluid containing or receiving device such as a receptacle or syringe barrel. Accordingly, the terms "syringe," "plunger rod assembly" and "plunger tip" are intended to be construed broadly to include a device having the characteristics or features described above. There is shown in the drawings and will herein be described in detail the currently preferred embodiments of the present invention with the understanding that the present disclosure is considered to be exemplary of the principles of the invention and is not intended to limit the scope of the invention to the embodiments described herein. The scope of the invention will be measured by the appended claims and their equivalents.

In describing the invention, the "distal end" or "distal portion" of a part or member is intended to refer to the end or portion which is positioned closest to the patient during use of the device. The terms "proximal" and or "proximal portion" of a part or member is intended to refer to the end or portion of a part or member which is positioned furthest from the patient during use of the device.

Figures 1, 8:
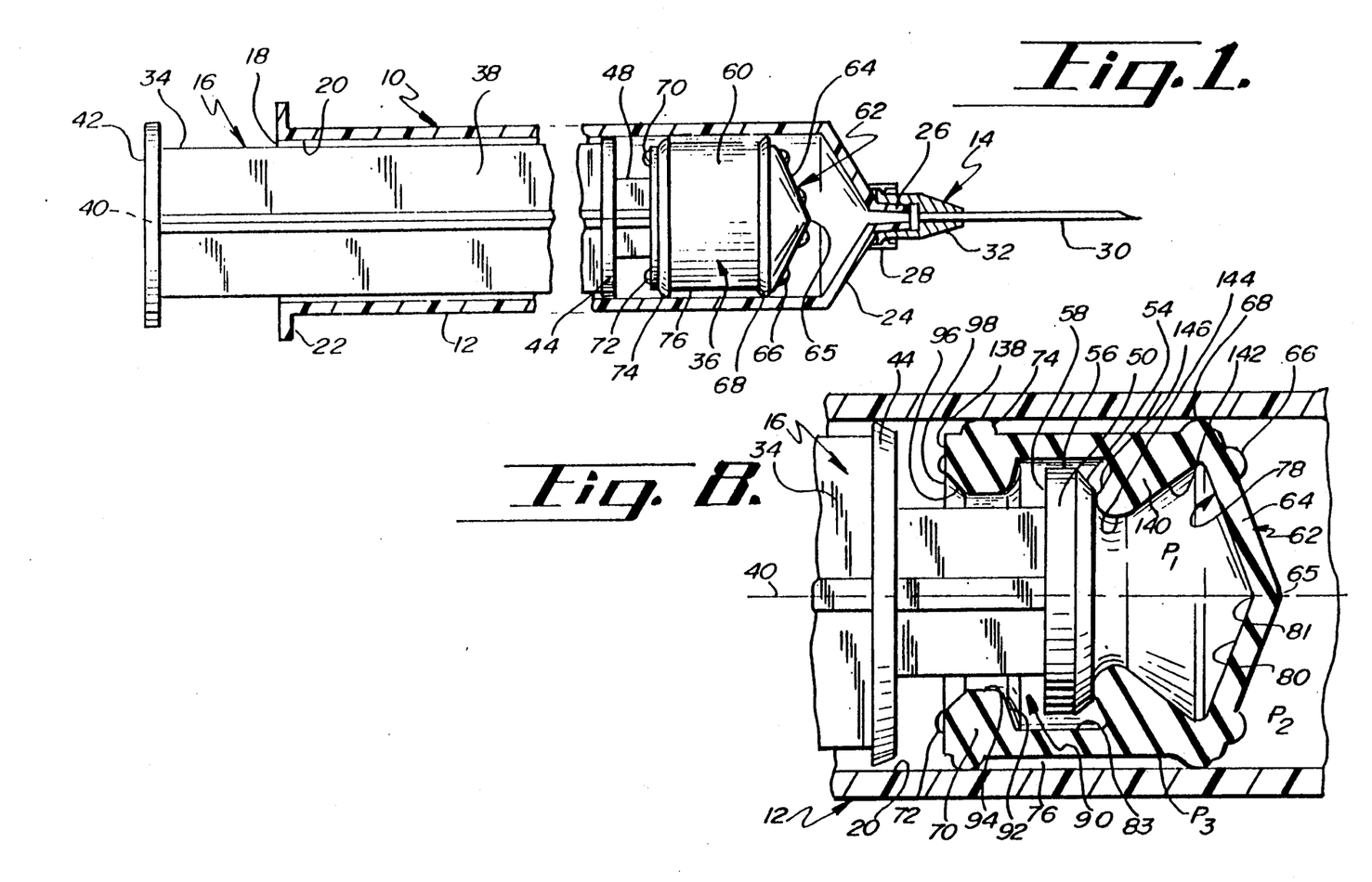
FIG. 1 is a side elevation view of the preferred plunger rod assembly of the present invention shown in a cross-sectioned view of a syringe barrel.
FIG. 8 is a cross-sectional view of a further alternate embodiment of the plunger tip of the present invention.

As shown in the drawings, the present invention preferably forms part of a syringe assembly 10. The syringe assembly 10 preferably includes an elongate and tubular syringe barrel 12, having a needle assembly 14 mounted thereon and a plunger rod assembly 16 received therein. As shown in FIG. 1, the syringe barrel 12 is an elongate and tubular member preferably made of a polypropylene or similar material. The proximal end 18 of the syringe barrel 12 is preferably open to the interior surface 20 of the syringe barrel 12 and includes an enlarged finger flange 22 extending radially outwardly therefrom. The distal end 24 of the syringe barrel 12 has a reduced diameter opening as compared to the interior surface 20 of the syringe barrel 12 and the opening at the proximal end 18 of the syringe barrel 12. A conically-shaped luer tip 26 extends from the distal end 24 of the syringe barrel 12 and a distally extending luer lock skirt 28 circumferentially surrounds the luer tip 26 on the distal end of the preferred syringe barrel 12.

The needle assembly 14 is preferably removably mounted on the distal end 24 of the syringe barrel 12. The needle assembly 14 preferably includes a cannula 30 having a sharpened distal needle point thereon and a hub member 32 on the proximal end thereof. The hub member 32 is designed to engage the luer tip 26 and luer skirt 28 on the distal end 24 of the syringe barrel 12 when the needle assembly 14 is mounted thereon.

As shown in the drawings, the plunger rod assembly 16 preferably consists of an elongate plunger rod 34 and a flexible plunger tip 36. The plunger rod includes an elongate shaft portion 38 defining a longitudinal axis 40. The proximal end of the plunger rod 34 includes an enlarged disc-shaped member which forms a thumb rest 42 thereon. An enlarged flange 44 is preferably located at the distal end of the shaft portion 38 of the plunger rod 34. This enlarged flange 44 is preferably a flat surface in a plane substantially perpendicular to the longitudinal axis 40 of the plunger rod 34. The diameter of this enlarged flange 44 is preferably slightly less than the diameter of the interior surface 20 of the syringe barrel and significantly less than the diameter of the thumb rest 42.

The distal portion 46 of the plunger rod 34 extends distally from the shaft portion 38 and enlarged flange 44 of the plunger rod 34. The distal portion 46 preferably includes a reduced neck portion 48 and a front flange 50. The diameter of the front flange 50 is greater than the diameter of the neck portion 48 and less than the diameter of the enlarged flange 44. The front flange 50 is preferably a circularly-shaped member and includes a flat distal surface 52 oriented in a plane substantially perpendicular to the longitudinal axis 40 of the plunger rod 34. A distally oriented tapered surface 54 intersects the distal surface 52 of the front flange 50 and preferably tapers outwardly from the intersection with the flat distal surface 52. The tapered surface 54 preferably extends along the longitudinal axis 40 of the plunger rod 34 to the side wall 56 of the front flange 50 to facilitate the insertion of the front flange 50 into the plunger tip 36 as described more fully below. The side wall 56 of the front flange 50 is substantially parallel to the longitudinal axis 40 of the plunger rod 34 and extends proximally from the tapered surface 54 to the proximal surface 58 of the front flange 50. The proximal surface 58 of the front flange 50 is substantially perpendicular to the longitudinal axis 40 of the plunger rod 34 and intersects the neck portion 48 of the plunger rod 34.

As shown in the drawings, the plunger tip 36 is a cylindrically-shaped flexible member which is preferably formed of an ethylene polypropylene or butyl rubber or other resilient material. The exterior surface 62 of the plunger tip 36 includes an annular side wall 60 which circumscribes a longitudinal axis that is identical to the longitudinal axis 40 of the plunger rod 34 when the plunger tip 36 is mounted thereon. The plunger tip 36 also includes a front wall 64 having an apex 65 thereon which intersects the longitudinal axis of the plunger tip 36. As partially shown in the drawings, a plurality of equally spaced apart stop members 66 are located on the front wall 64 of the plunger tip 36. An annular distal rib member 68 is formed on the side wall 60 proximally of the intersection of the front wall 64 and the side wall 60. An annular rear wall 70 is located at the proximal end of the plunger tip 36. The rear wall 70 preferably has a plurality of stop members 72 thereon and is oriented in a plane substantially perpendicular to the longitudinal axis of the plunger tip 36. An annular proximal rib member 74 is formed on the side wall 60 of the plunger tip 36 slightly distal of the intersection between the side wall 60 and the rear wall 70. The distal rib member 68 and the proximal rib member 74 are located on the plunger tip 36 such that an annular recessed area 76 which is formed therebetween and has a smaller circumference than the circumference of the distal or proximal rib members, 68 and 74, respectively.

The interior surface 78 of the plunger tip 36 extends distally through the rear wall 70 of the plunger tip 36 to the interior side 80 of the front wall 64. The interior side 80 of the front wall 64 is oriented in the same manner as the exterior surface 62 of the front wall 64 and includes an apex 81 on the longitudinal axis of the plunger tip 36. The intersection of the front wall 64 and the lip member 82 is preferably longitudinally aligned with the distal rib member 68 on the exterior surface 62 of the side wall 60. An inwardly and proximally directed flexible annular lip member 82 is located proximally of the front wall 64 in the interior surface 78 of the plunger tip 36. The lip member 82 includes a distal surface 84 extending proximally from the interior surface 78 of the front wall 64 at an acute angle, preferably from about 25 to 45 degrees from the longitudinal axis of the plunger tip 36 and more preferably about 30 degrees from the longitudinal axis of the plunger tip 36. The distal surface 84 of the lip member 82 extends proximally along the lip member 82 to a generally flat surface 86 which is generally parallel to the longitudinal axis of the plunger tip 36. The flat surface 86 extends proximally from the distal surface 84 to a proximal surface 88 which extends radially outwardly and distally therefrom towards the side wall 60 of the plunger tip 36 to form an undercut area radially outwardly from the lip member 82. The proximal surface 88 of the plunger tip 36 is oriented at an angle of about 45 degrees to 70 degrees from the longitudinal axis of the plunger tip 36 and more preferably at an angle of about 65 degrees from the longitudinal axis of the plunger tip 36 such that the thickness of the lip member 82 increases slightly from the innermost portion of the lip member 82 towards the exterior surface 62 of the plunger tip 36. The flat surface 86 of the lip member 82 is preferably located approximately midway between the distal and proximal rib members, 68 and 74, respectively. The intersection of the flat surface 86 and the proximal surface 88 is preferably located slightly closer to the proximal rib member 74 than the distal rib member 68 while the intersection of the flat surface 86 and the distal surface 84 is preferably located lightly closer to the distal rib member 68 than the proximal rib member 74.

A plunger rod receiving area 90 is formed by the interior sidewall surface 33 of the side wall 60 between the lip member 82 and the rear wall 70 of the plunger tip 36. The rear wall 70 includes a distal surface 92 which is slightly tapered and is oriented nearly perpendicular to the longitudinal axis of the plunger tip 36 as shown in the drawings. A flat surface 94 extends proximally from the distal surface 92 of the rear wall 70 and is oriented generally parallel to the longitudinal axis of the plunger tip 36. The flat surface 94 of the rear wall 70 includes a proximal tapered surface 96 thereon which tapers radially outwardly from the flat surface 94 to the proximal surface 98 of the rear wall 70 to facilitate the insertion of the front flange 50 of the plunger rod 34 into the plunger rod receiving area 90 of the plunger tip 36. The diameter of the rear wall 70 along the flat surface 94 is preferably less than the diameter of the plunger rod receiving area 90 and greater than the diameter of the flat surface of the lip member 82 to retain the front flange 50 of the plunger rod 34 in the plunger rod receiving area 90.

Figure 3:
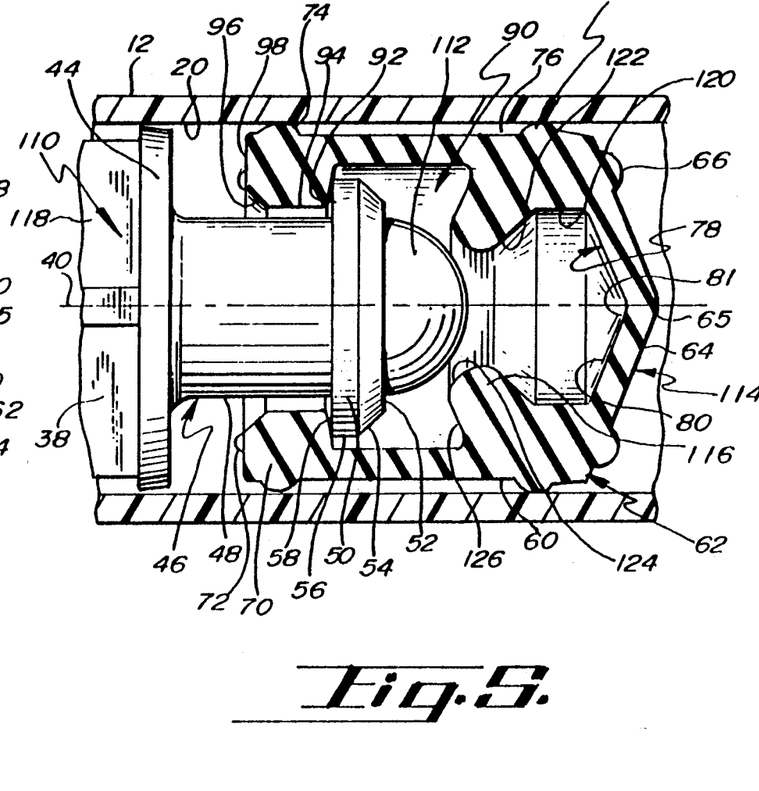
FIG. 3 is a partial cross-sectional view of the preferred plunger rod assembly in a cross-sectional portion of a syringe barrel illustrating the expansion of the plunger tip in response to a proximally directed force on the plunger rod wherein the various forces on the plunger rod assembly are diagrammatically indicated.
Figure 4:
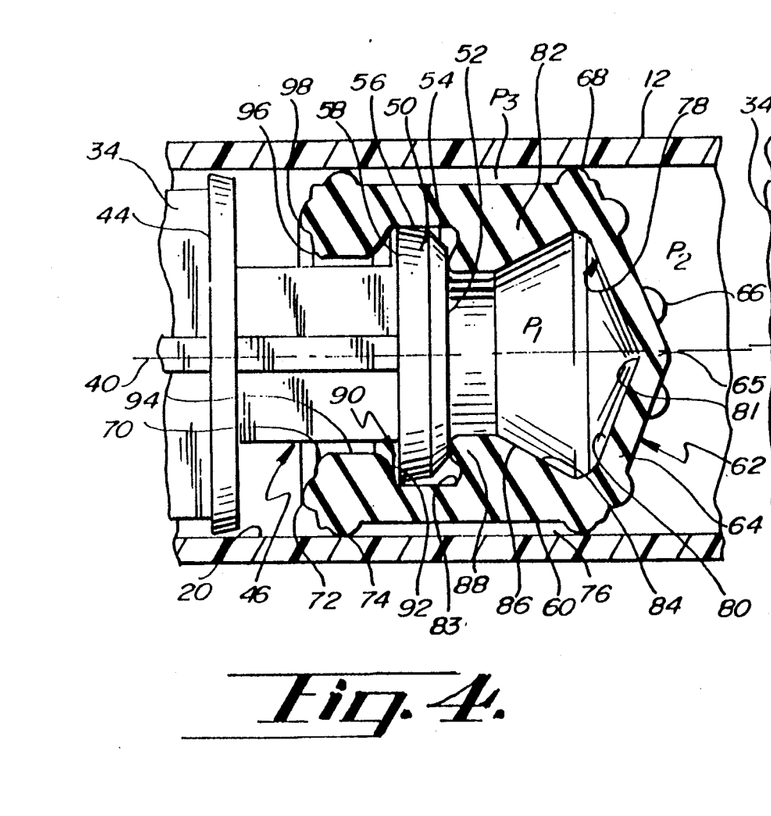
FIG. 4 is a partial cross-sectional view of the preferred plunger rod assembly in a cross-sectional portion of a syringe barrel illustrating the expansion of the plunger tip in response to a distally directed force on the plunger rod wherein the various forces on the plunger rod assembly are diagrammatically indicated.

To assist in understanding the preferred form of the present invention, FIGS. 3 and 4 include areas designated as $P_1$, $P_2$ and $P_3$ to designate pressures at the various locations shown in the drawings. $P_1$ is intended to reflect the pressure in the interior of the plunger tip 36 and distally of the lip member 82 and plunger rod receiving area 90. This pressure is usually equal to atmospheric pressure. $P_2$ is intended to reflect the pressure in the interior of the syringe barrel 12 between the distal end of the plunger tip 36 and the distal end 24 of the syringe barrel 12. $P_3$ is intended to reflect the pressure in the annular recess area 76 between the distal and proximal rib members, 68 and 74, respectively.

Figure 2:
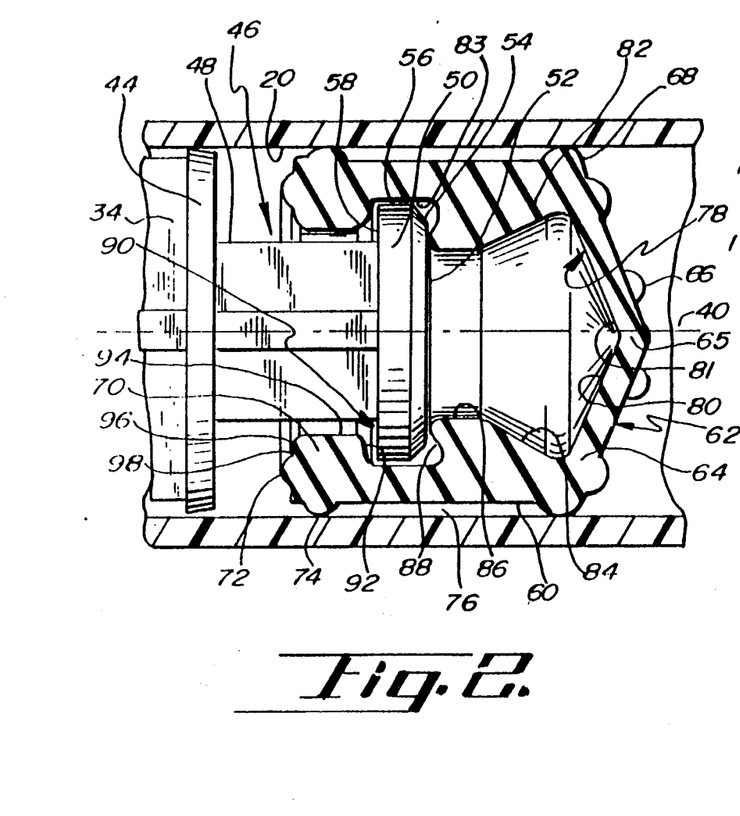
FIG. 2 is a partial cross-sectional view showing the preferred plunger rod assembly of FIG. 1 in a portion of a syringe barrel.

In the preferred use of the present embodiment, the syringe assembly 10 includes a needle assembly 14 thereon and the plunger rod assembly 16 is initially positioned adjacent to the distal end 24 of the syringe barrel 12. When the user desires to use the present invention to obtain an arterial blood gas sample from a patient, the pressure of the blood in the artery of the patient will oftentimes be sufficient to move the plunger rod assembly 16 proximally in the syringe barrel 12. The present invention is designed to have a reduced frictional resistance to movement of the plunger rod assembly 16 due to the reduced frictional contact between the distal and proximal rib members, 68 and 74, respectively, and the interior surface 20 of the syringe barrel 12 when the plunger rod 34 is at rest (FIG. 2) and therefore, the force required for the arterial blood sample to move the plunger rod assembly 16 is less than in a conventional syringe.

When the arterial blood pressure of the patient is sufficient to move the plunger tip 36 proximally in the syringe barrel 12, the pressure in the interior of the plunger tip 36 ($P_1$) and the pressure in the annular recess area 76 ($P_3$) are approximately equal and the pressure in the distal end of the syringe barrel 12 ($P_2$) is greater than the pressure of either $P_1$ or $P_3$. The front wall 64 of the plunger tip 36 is shaped so that the pressure applied thereto ($P_2$) by the arterial blood of the patient will be distributed evenly along the exterior surface 62 of the front wall 64 so that the front wall 64 will not flex significantly in response to the arterial pressure and therefore the contact between the distal rib member 68 and the interior surface 20 of the syringe barrel 12 will not be significantly increased.

As shown in FIG. 3, when the user desires to aspirate or move the plunger rod assembly 16 proximally in the syringe barrel 12 to obtain a blood sample or receive a medication in the syringe barrel 12, the present invention utilizes the interaction and contact between the plunger rod 34 and plunger tip 36 and also the differences between the various pressures created in the syringe barrel 12 to increase the seal between the proximal rib member 74 on the plunger tip 36 and the interior surface 20 of the syringe barrel 12. As shown in FIG. 3, when the plunger rod 34 is moved proximally in the syringe barrel 12, the proximal surface 58 of the front flange 50 on the plunger rod 34 contacts the distal surface 92 of the rear wall 70 on the plunger tip 36. Because of the frictional resistance between the proximal rib member 74 and the interior surface 20 of the syringe barrel 12 and the slight taper of the distal surface 92 of the rear wall 70 (approximately 10 degrees), the proximal force of the plunger rod 34 causes the rear wall 70 to flex outwardly. Therefore, the outward flexing of the rear wall 70 caused by the plunger rod 34 increases the seal between the proximal rib member 74 and the interior surface 20 of the syringe barrel 12.

As shown diagrammatically in FIG. 3, the proximal movement of the plunger rod 34 also causes the front wall 64 of the plunger tip 36 to flex or stretch distally due to the various pressures acting on the front wall 64 of the plunger tip 36. When the plunger rod assembly 16 is moved proximally in the syringe barrel 12, the pressure distally of the plunger tip 36 ($P_2$) is significantly less than the pressure in the interior of the plunger tip 36 ($P_1$). This difference in the respective pressures causes the front wall 64 of the plunger tip 36 to flex distally thereby moving the apex 65 distally in the syringe barrel 12 as compared to the remainder of the plunger tip 36. This causes the distal portion of the plunger tip 36 to be elongated in the syringe barrel 12. The distal movement of the front wall 64 causes the distal rib member 68 to apply less pressure to the interior surface 20 of the syringe barrel 12 so that the sealing pressure between the distal rib member 68 and the syringe barrel 12 is reduced or broken while still providing alignment and stability to the plunger tip 36. When this occurs, the pressure in the annular recess area 76 ($P_3$) is also reduced slightly with respect to the pressure in the interior of the plunger tip 36 ($P_1$). This difference in pressure between $P_1$ and $P_3$ is believed to cause the proximal portion of the plunger tip 36 to expand which further increases the sealing pressure between the proximal rib member 74 and the interior surface 20 of the syringe barrel 12.

As shown in FIG. 4, when the user desires to expel fluid from the syringe barrel 12, the preferred form of the present invention utilizes the interaction and contact between the plunger rod 34 and plunger tip 36 and also the differences between the various pressures created in the syringe barrel 12 to increase the seal between the distal rib member 68 on the plunger tip 36 and the interior surface 20 of the syringe barrel 12. As shown in FIG. 4, when the plunger rod 34 is moved distally in the syringe barrel 12, the flat distal surface 52 on the front flange 50 of the plunger rod 34 contacts and causes the proximal surface 88 of the lip member 82 to flex in response to the force applied thereto by the plunger rod 34. The lip member 82 is particularly shaped such that the distally directed force applied thereto by the plunger rod 34 causes the proximal surface 88 of the lip member 82 to flex in response to the force applied thereto by the distal surface 52 of the front flange 50. This force is then transferred through the lip member 82 to the intersection of the front wall 64 and the lip member 82 and then to the distal rib member 68 to radially expand the distal rib member 68 against the interior surface 20 of the syringe barrel 12. Therefore, the force applied by the user to the plunger rod 34 is indirectly applied to the distal rib member 68 through the lip member 82 and the larger the force applied by the user to the plunger rod 34, the greater the flexing and deformation of the proximal surface 88 of the lip member 82 will be so that the seal between the distal rib member 68 against the interior surface 20 of the syringe barrel 12 will be similarly increased.

When fluid is expelled from the syringe assembly 10, the various pressures identified in FIG. 4 also contribute to the sealing of the distal rib member 68 and the interior surface 20 of the syringe barrel 12. As diagrammatically shown in FIG. 4, when fluid is expelled from the syringe barrel 12, the pressure distally of the plunger tip 36 ($P_2$) is significantly greater than the pressure in the interior of the plunger tip 36 ($P_1$) or in the annular recess area 76 ($P_3$). The difference in pressure between $P_1$ and $P_2$ causes the front wall 64 of the plunger tip 36 to flex proximally as the plunger tip 36 is moved distally in the syringe barrel 12. The shape and thickness of the front wall 64 causes the force applied to the front wall 64 by $P_2$ to increase the radial diameter of the distal rib member 68 thereby increasing the sealing pressure between the distal rib member 68 and the interior surface 20 of the syringe barrel 12.

Figure 6:
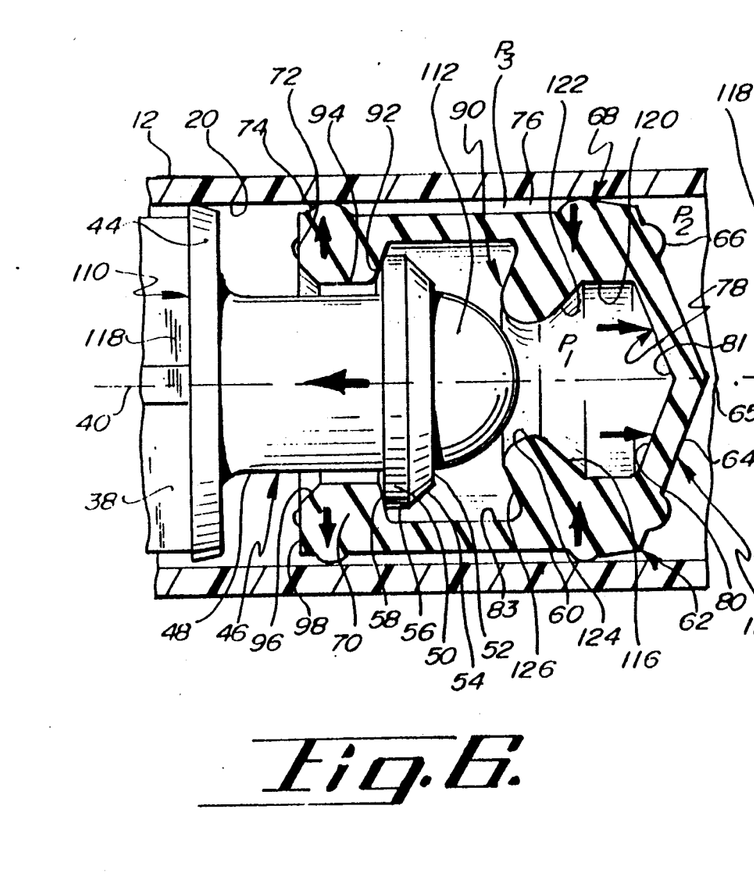
FIG. 6 is a partial cross-sectional view of the alternate embodiment of the plunger rod assembly of FIG. 5 illustrating the expansion of the plunger tip in response to a proximally directed force on the plunger rod wherein the various forces on the plunger rod assembly are diagrammatically indicated.
Figure 7:
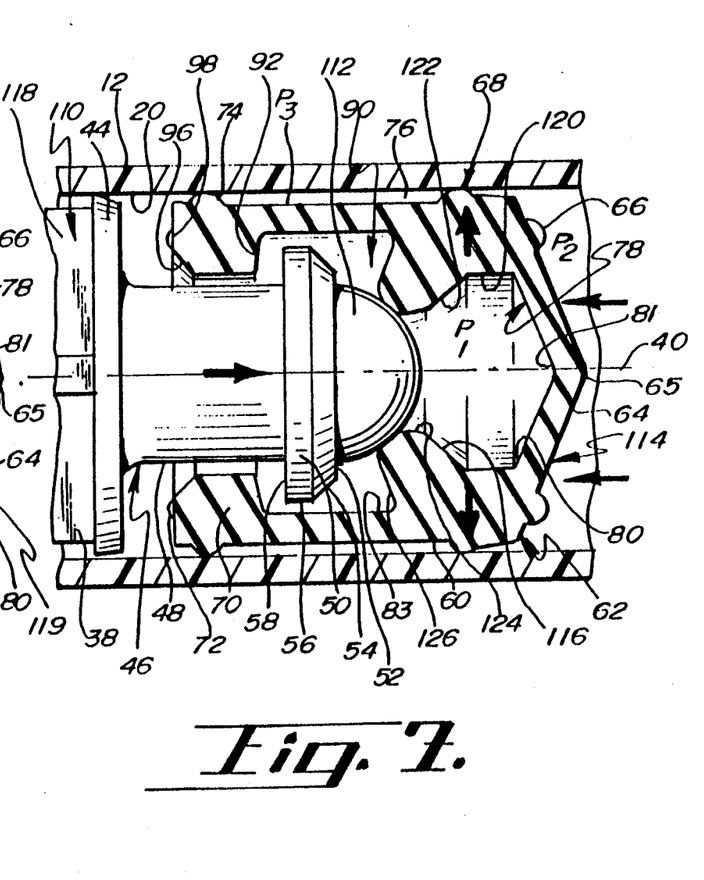
FIG. 7 is a partial cross-sectional view of the alternate embodiment of the plunger rod assembly of FIG. 5 illustrating the expansion of the plunger tip in response to a distally directed force on the plunger rod wherein the various forces on the plunger rod assembly are diagrammatically indicated.

FIGS. 5-7 illustrate a further embodiment of the present invention wherein the plunger rod assembly 110 has been modified to include a bulbous or semicircularly-shaped contact member 112 extending distally from the distal surface 52 of the front flange 50. As shown in the drawings, the plunger tip 114 of the plunger rod assembly 110 has also been modified to include a modified lip member 116. As with the prior embodiment, the present embodiment includes a syringe barrel 12 and a needle assembly as shown and described above.

The plunger rod assembly 110 of the present embodiment preferably consists of an elongate plunger rod 118 and a flexible plunger tip 114. The plunger rod 118 includes an elongate shaft portion 38 defining a longitudinal axis 40. The proximal end of the plunger rod 118 includes an enlarged disc-shaped member which forms a thumb rest (not shown) thereon. An enlarged flange 44 is preferably located at the distal end of the shaft portion 38 of the plunger rod 118. This enlarged flange 44 is preferably a flat surface in a plane substantially perpendicular to the longitudinal axis 40 of the plunger rod 118. The diameter of this enlarged flange 44 is preferably slightly less than the diameter of the interior surface 20 of the syringe barrel and significantly less than the diameter of the thumb rest.

The distal portion 46 of the plunger rod 118 extends distally from the shaft portion 38 and enlarged flange 44 of the plunger rod 118. The distal portion 46 preferably includes a reduced neck portion 48 and a front flange 50. The diameter of the front flange 50 is greater than the neck portion 48 and less than the diameter of the enlarged flange 44. The front flange 50 is preferably a circularly-shaped member and includes a distal surface 52 having a semicircularly-shaped contact member 112 thereon. A distally oriented tapered surface 54 intersects the distal surface 52 of the front flange 50 and preferably tapers outwardly from the intersection with the flat distal surface 52. The tapered surface 54 preferably extends along the longitudinal axis 40 of the plunger rod 118 to the side wall 56 of the front flange 50 to facilitate the insertion of the front flange 50 into the plunger tip 114 as described more fully below. The side wall 56 of the front flange 50 is substantially parallel to the longitudinal axis 40 of the plunger rod 118 and extends proximally from the tapered surface 54 to the proximal surface 58 of the front flange 50. The proximal surface 58 of the front flange 50 is substantially perpendicular to the longitudinal axis 40 of the plunger rod 118 and intersects the neck portion 48 of the plunger rod 118.

As shown in the drawings, the plunger tip 114 is a cylindrically-shaped flexible member which is preferably formed of a ethylene polypropylene rubber or other resilient material. The exterior surface 62 of the plunger tip 114 includes an annular side wall 60 which circumscribes a longitudinal axis that is identical to the longitudinal axis 40 of the plunger rod 118 when the plunger tip 114 is mounted thereon. The plunger tip 114 also includes a front wall 64 having an apex 65 thereon which intersects the longitudinal axis of the plunger tip 114. As partially shown in the drawings, a plurality of equally spaced apart stop members 66 are located on the front wall 64 of the plunger tip 114. An annular distal rib member 68 is formed on the side wall 60 proximally of the intersection of the front wall 64 and the side wall 60. As shown in the drawings, the distal rib member 68 of the present embodiment is positioned further from the front wall 64 of the plunger tip 114 than in the preferred embodiment. An annular rear wall 70 is located at the proximal end of the plunger tip 114. An annular proximal rib member 74 is formed on the side wall 60 of the plunger tip 114 slightly distal of the intersection between the side wall 60 and the rear wall 70. The distal rib member 68 and the proximal rib member 74 are located on the plunger tip 114 such that an annular recessed area 76 which is formed therebetween has a smaller circumference than the circumference of the distal or proximal rib members, 68 and 74, respectively.

The interior surface 78 of the plunger tip 114 extends distally through the rear wall 70 of the plunger tip 114 to the interior side 80 of the front wall 64. The interior side 80 of the front wall 64 is oriented in the same manner as the exterior surface 62 of the front wall 64 and includes an apex 81 on the longitudinal axis of the plunger tip 114. The inwardly and proximally directed flexible annular lip member 116 is located proximally of the front wall 64 in the interior surface 78 of the plunger tip 114. The intersection of the front wall 64 and the lip member 116 of this embodiment are spaced apart by a generally flat surface 120. The intersection of the flat surface 120 and the distal surface 122 of the lip member 116 is preferably longitudinally aligned with the distal rib member 68 on the exterior surface 62 of the side wall 60. The lip member 116 includes the distal surface 122 extending proximally from the flat surface 120 of the plunger tip 114 preferably at an acute angle of about 25 to 45 degrees from the longitudinal axis of the plunger tip 114 and more preferably about 30 degrees from the longitudinal axis of the plunger tip 114. The distal surface 122 of the lip member 116 extends proximally along the lip member 116 to a generally semicircularly-shaped surface 124. The semicircularly-shaped surface 124 extends proximally from the distal surface 122 to a proximal surface 126 which extends radially outwardly and distally therefrom towards the side wall 60 of the plunger tip 114 to form an undercut area radially outwardly from the lip member 116. The proximal surface 126 of the plunger tip 114 is oriented at an angle of about 45 degrees to 70 degrees from the longitudinal axis of the plunger tip 114 and more preferably at an angle of about 65 degrees from the longitudinal axis of the plunger tip 114 such that the thickness of the lip member 116 increases slightly from the innermost portion of the lip member 116 towards the exterior surface 62 of the plunger tip 114. The intersection of the flat surface 120 and the distal surface 122 of the lip member 116 is preferably located in approximate alignment with the distal rib member 68. The semicircular surface 124 is preferably located closer to the distal rib member 68 in the present embodiment than in the preferred embodiment and the flat surface 120 of this embodiment is preferably thicker than the intersection of the distal surface 84 and front wall 64 of the preferred embodiment such that forces applied to the lip member 116 of the present embodiment are applied more directly to the distal rib member 68 than in the preferred embodiment.

The plunger rod receiving area 90 is formed by the interior sidewall surface 83 of the side wall 60 between the lip member 116 and the rear wall 70 of the plunger tip 114. The rear wall 70 includes a distal surface 92 which is slightly tapered and is oriented nearly perpendicular to the longitudinal axis of the plunger tip 114 as shown in the drawings. As in the preferred embodiment, a flat surface 94 extends proximally from the distal surface 92 of the rear wall 70 and is oriented generally parallel to the longitudinal axis of the plunger tip 114. The flat surface 94 of the rear wall 70 includes a proximal tapered surface 96 thereon which tapers radially outwardly from the flat surface 94 to the proximal surface 98 of the rear wall 70 to facilitate the insertion of the front flange 50 of the plunger rod 118 into the plunger rod receiving area 90 of the plunger tip 114. The diameter of the rear wall 70 along the flat surface 94 is preferably less than the diameter of the plunger rod receiving area 90 and greater than the diameter of the flat surface of the lip member 116 to retain the front flange 50 of the plunger rod 118 in the plunger rod receiving area 90.

To assist in understanding the present embodiment, FIGS. 6 and 7 include areas designated as $P_1$, $P_2$ and $P_3$ to designate pressures at the various locations shown in the drawings. $P_1$ is intended to reflect the pressure in the interior of the plunger tip 114 and distally of the lip member 116 and plunger rod receiving area 90. This pressure is usually equal to atmospheric pressure. $P_2$ is intended to reflect the pressure in the interior of the syringe barrel 12 between the distal end of the plunger tip 114 and the distal end 24 of the syringe barrel 12. $P_3$ is intended to reflect the pressure in the annular recess area 76 between the distal and proximal rib members, 68 and 74, respectively. In the preferred use of this alternate embodiment, the syringe assembly 10 includes a needle assembly 14 thereon and the plunger rod assembly 110 is initially positioned adjacent to the distal end 24 of the syringe barrel 12. When the user desires to use the present invention to obtain an arterial blood gas sample from a patient, the pressure of the blood in the artery of the patient will usually be sufficient to move the plunger rod assembly 110 proximally in the syringe barrel 12. The present invention is designed to have a reduced frictional resistance to movement of the plunger rod assembly 110 due to the reduced frictional contact between the distal and proximal rib members, 68 and 74, respectively, and the interior surface 20 of the syringe barrel 12 when the plunger rod 118 is at rest (FIG. 5) and therefore, the force required for the arterial blood sample to move the plunger rod assembly 110 is less than in a conventional syringe.

When the arterial blood pressure of the patient is sufficient to move the plunger tip 114 proximally in the syringe barrel 12, the pressure in the interior of the plunger tip 114 ($P_1$) and the pressure in the annular recess area 76 ($P_3$) are approximately equal and the pressure in the distal end of the syringe barrel 12 ($P_2$) is greater than the pressure of either $P_1$ or $P_3$. The front wall 64 of the plunger tip 114 is shaped so that the pressure applied thereto ($P_2$) by the arterial blood of the patient will be distributed evenly along the exterior surface 62 of the front wall 64 so that the front wall 64 will not flex significantly in response to the arterial pressure and therefore the contact between the distal rib member 68 and the interior surface 20 of the syringe barrel 12 will not be significantly increased.

As shown in FIG. 6, when the user desires to aspirate or move the plunger rod assembly 110 proximally in the syringe barrel 12 to obtain a blood sample or receive a medication in the syringe barrel 12, the present invention utilizes the interaction and contact between the plunger rod 118 and plunger tip 114 and also the differences between the various pressures created in the syringe barrel 12 to increase the seal between the proximal rib member 74 on the plunger tip 114 and the interior surface 20 of the syringe barrel 12. As shown in FIG. 6, when the plunger rod 118 is moved proximally in the syringe barrel 12, the proximal surface 58 of the front flange 50 on the plunger rod 118 contacts the distal surface 92 of the rear wall 70 on the plunger tip 114. Because of the frictional resistance between the proximal rib member 74 and the interior surface 20 of the syringe barrel 12 and the slight taper of the distal surface 92 of the rear wall 70 (approximately 10 degrees), the proximal force of the plunger rod 118 causes the rear wall 70 to flex outwardly. Therefore, the outward flexing of the rear wall 70 caused by the plunger rod 118 increases the seal between the proximal rib member 74 and the interior surface 20 of the syringe barrel 12.

As shown diagrammatically in FIG. 6, the proximal movement of the plunger rod 118 also causes the front wall 64 of the plunger tip 114 to flex or stretch distally due to the various pressures acting on the front wall 64 of the plunger tip 114. When the plunger rod assembly 110 is moved proximally in the syringe barrel 12, the pressure distally of the plunger tip 114 ($P_2$) is significantly less than the pressure in the interior of the plunger tip 114 ($P_1$). This difference in the respective pressures causes the front wall 64 of the plunger tip 114 to flex distally thereby moving the apex 65 distally in the syringe barrel 12 as compared to the remainder of the plunger tip 114. This causes the distal portion of the plunger tip 114 to be elongated in the syringe barrel 12. The distal movement of the front wall 64 causes the distal rib member 68 to apply less pressure to the interior surface 20 of the syringe barrel 12 so that the sealing pressure between the distal rib member 68 and the syringe barrel 12 is reduced or broken while still providing alignment and stability to the plunger tip 114. When this occurs, the pressure in the annular recess area 76 ($P_3$) is also reduced slightly with respect to the pressure in the interior of the plunger tip 114 ($P_1$). This difference in pressure between $P_1$ and $P_3$ is believed to cause the proximal portion of the plunger tip 114 to expand which further increases the sealing pressure between the proximal rib member 74 and the interior surface 20 of the syringe barrel 12.

As shown in FIG. 7, when the user desires to expel fluid from the syringe barrel 12, the alternate embodiment of the present invention utilizes the interaction and contact between the plunger rod 118 and plunger tip 114 and also the differences between the various pressures created in the syringe barrel 12 to increase the seal between the distal rib member 68 on the plunger tip 114 and the interior surface 20 of the syringe barrel 12. As shown in FIG. 7, when the plunger rod 118 is moved distally in the syringe barrel 12, the contact member 112 on the front flange 50 of the plunger rod 118 contacts and causes the semicircular surface 124 of the lip member 116 to flex in response to the force applied thereto by the plunger rod 118. The lip member 116 is particularly shaped such that the distally directed force applied thereto by the plunger rod 118 causes the semicircular surface 124 of the lip member 116 to flex in response to the force applied thereto by the contact member 112 of the front flange 50. This force is then transferred through the lip member 116 to the distal rib member 68 to radially expand the distal rib member 68 against the interior surface 20 of the syringe barrel 12. In this embodiment, the thickness of the plunger tip 114 between the flat surface 120 and the exterior surface 62 of the plunger tip 114 resists deformation by the lip member 116 so that the force applied by the plunger rod 118 to the lip member 116 is more directly applied to the distal rib member 68 than in the preferred embodiment. The larger the force applied by the user to the plunger rod 118, the greater the flexing and deformation of the semicircular surface 124 of the lip member 116 will be so that the seal between the distal rib member 68 against the interior surface 20 of the syringe barrel 12 will be similarly increased. In this embodiment, the area of contact between the contact member 112 on the plunger rod 118 and the semicircular surface 124 on the lip member 116 will vary according to the amount of force applied to the distal rib member 68 of the plunger rod 118 so that the direction of the force by this contact will become more direct as the force is increased.

When fluid is expelled from the syringe assembly 10, the various pressures identified in FIG. 7 also contribute to the sealing of the distal rib member 68 and the interior surface 20 of the syringe barrel 12. As diagrammatically shown in FIG. 7, when fluid is expelled from the syringe barrel 12, the pressure distally of the plunger tip 114 ($P_2$) is significantly greater than the pressure in the interior of the plunger tip 114 ($P_1$) or in the annular recess area 76 ($P_3$). The difference in pressure between $P_1$ and $P_2$ causes the front wall 64 of the plunger tip 114 to flex proximally as the plunger tip 114 is moved distally in the syringe barrel 12. The shape and thickness of the front wall 64 causes the force applied to the front wall 64 by $P_2$ to indirectly increase the radial diameter of the distal rib member 68 thereby increasing the sealing pressure between the distal rib member 68 and the interior surface 20 of the syringe barrel 12.

FIG. 8 illustrates a further alternate embodiment of the plunger tip 138 of the present invention which may be used with either of the plunger rod assemblies 16 or 110 described above. In this embodiment, the lip member 140 has been modified to include a distal surface 142; a semicircular surface 144 and a proximal surface 146 similar to those described above with respect to the alternate embodiment. The lip member 140 is positioned in the interior of the plunger tip 138 in a manner similar to that described above with respect to the preferred embodiment. The function of this embodiment is similar to the function of the preferred embodiment described above and therefore will not be repeated herein.

In the present invention, the shape of the front wall 64 also causes the force located distally of the front wall 64 ($P_2$) to be distributed equally along the exterior surface 62 of the front wall 64 thereby ensuring that the seal between the distal rib member 68 and the interior surface 20 of the syringe barrel 12 will be uniformly increased around the circumference of the plunger tip as fluid is expelled from the syringe barrel 12. Additionally, the relative size of the plunger rod receiving area 90 in the plunger tip ensures that contact will be maintained between the distal surface 52 of the plunger rod and the lip member of the plunger tip even if the user offsets or cants the plunger rod with respect to the longitudinal axis 40 of the plunger rod as fluids are expelled from the syringe barrel 12.

What is claimed is:

1. A plunger rod assembly for use with a cylindrical barrel member having a longitudinal axis and an interior surface and provided with an open proximal end to receive the plunger rod assembly therethrough and a distal end adapted to receive or deliver fluid therethrough, said plunger rod assembly comprising:
    a plunger rod including a rigid elongate shaft portion and a front flange on the distal end thereof; and
    a flexible plunger tip operatively mounted on said front flange, said plunger tip including front and side walls and interior and exterior surfaces and a lip member which extends radially inwardly from said interior surface of said side wall, said lip member being oriented in such a manner on said side wall so that movement of said plunger rod causes said front flange to operatively contact said lip member to radially expand at least a portion of said plunger tip.

2. The plunger rod assembly of claim 1 wherein said lip member extends radially inwardly and proximally from said side wall of said plunger tip.

3. The plunger rod assembly of claim 1 wherein said front flange of said plunger rod includes a distal surface having a generally flat contact surface thereon.

4. The plunger rod assembly of claim 1 wherein said front flange of said plunger rod includes a distal surface having a generally semicircularly-shaped contact member thereon.

5. The plunger rod assembly of claim 1 wherein said plunger tip includes a plunger rod receiving area in the interior thereof and wherein said plunger rod receiving area receives said front flange therein and is sized to allow said plunger rod to be laterally offset from the longitudinal axis of the barrel member while maintaining the contact between said front flange and said lip member and said plunger tip and the interior surface of the barrel member.

6. The plunger rod assembly of claim 1 wherein said front wall of said plunger tip is sized to flex in response to distal movement of said plunger tip in the barrel member to increase the radial diameter of at least a portion of said plunger tip.

7. The plunger rod assembly of claim 1 wherein said plunger tip includes a rear wall thereon and wherein said rear wall is sized to receive a portion of said plunger rod therethrough, said rear wall being oriented to contact a proximal surface on said front flange of said plunger rod upon proximal movement of said plunger rod in the barrel member in such a manner that at least a portion of said plunger tip is radially expanded.

8. The plunger rod assembly of claim 7 wherein said front wall of said plunger tip is sized to flex in response to proximal movement of said plunger tip in the barrel member to reduce the diameter of a further portion of said plunger tip.

9. A plunger rod assembly for use with a cylindrical barrel member having a longitudinal axis and an interior surface and provided with an open proximal end and a distal end adapted to receive or deliver fluid therethrough, said plunger rod assembly comprising:
    an elongate plunger rod means including a shaft portion adapted to extend through the proximal end of the barrel member and further including a front flange on the distal end thereof;
    a flexible plunger tip operatively mounted about said front flange, said plunger tip including front, rear and side walls with interior and exterior surfaces wherein said rear wall is sized to receive at least a portion of said plunger rod means therethrough; and
    a lip member extending radially inwardly and proximally from said interior surface of said side wall of said plunger tip wherein said lip member is sized to operatively contact said front flange and radially expand at least a portion of said plunger tip as said plunger rod means is moved distally through the barrel member.

10. The plunger rod assembly of claim 9 wherein said plunger tip includes a rib member circumferentially along said exterior surface of said plunger tip and said rib member forms a fluid tight seal between said plunger tip and the interior surface of the barrel member.

11. The plunger rod assembly of claim 9 wherein said plunger tip includes distal and proximal circumferential rib members thereon and wherein distal movement of said plunger rod means in the barrel member causes said distal rib member to radially expand and proximal movement of said plunger rod means in the barrel member causes said proximal rib member to radially expand.

12. The plunger rod assembly of claim 9 wherein said front wall of said plunger tip is sized to cause at least a portion of said plunger tip to radially expand as said plunger rod means is moved distally through the barrel member.

13. The plunger rod assembly of claim 9 wherein said front flange includes distal contact surface thereon which is generally perpendicular to the longitudinal axis of the barrel member thereon and which is sized to contact said lip member as said plunger rod means is moved distally through the barrel member.

14. The plunger rod assembly of claim 9 wherein said front flange includes a proximal surface thereon which is oriented generally perpendicular of the longitudinal axis of the barrel member and is sized to contact the rear wall of the plunger tip to cause the radial expansion of at least a portion of said plunger tip as said plunger rod means is moved proximally through the barrel member.

15. The plunger rod assembly of claim 9 wherein said front wall of said plunger tip is sized to cause the radial expansion of at least a portion of said plunger tip in response to the distal movement of said plunger rod means in the barrel member and to decrease the radial diameter of at least a portion of said plunger tip in response to the proximal movement of said plunger rod means in the barrel member.

16. The plunger rod assembly of claim 9 wherein said plunger tip includes a plunger rod receiving area in said interior of said plunger tip wherein said plunger rod receiving area is sized to receive said front flange therein in a spaced apart relationship with said side walls of said plunge tip.

17. The plunger rod assembly of claim 9 wherein said front flange of said plunger rod means includes a distal surface thereon and said distal surface is a semicircularly-shaped contact member which is sized to contact said lip member as said plunger rod means is moved distally through the barrel member.

18. A plunger rod assembly for use with a cylindrical barrel member having a longitudinal axis and an interior surface and provided with an open proximal end and a distal end adapted to receive or deliver fluid therethrough, said plunger rod assembly comprising:
  an elongate plunger rod including a shaft portion adapted to extend through the proximal end of the barrel member and a front flange on the distal end thereof;
  a flexible plunger tip operatively mounted on said front flange, said plunger tip including front, rear and side walls with interior and exterior surfaces wherein said rear wall is sized to receive at least a portion of said plunger rod therethrough; and
  a lip member extending radially inwardly and proximally from said interior surface of said side wall of said plunger tip wherein said lip member is sized to operatively contact said front flange and radially expand at least a portion of said plunger tip as said plunger rod is moved distally through the barrel member; and
  wherein said plunger tip includes distal and proximal rib members circumferentially along said exterior surface of said plunger tip and said rib members form a fluid tight seal between said plunger tip and the interior surface of the barrel member with said distal rib member being positioned about said plunger tip to form the primary seal between said plunger tip and the barrel member when said plunger rod is moved distally in the barrel member and said proximal rib member is positioned about said plunger tip to form the primary seal between said plunger tip and the barrel member when said plunger rod is moved proximally in the barrel member.

19. The plunger rod assembly of claim 18 wherein said front flange includes a distal surface thereon which is sized to contact said lip member and is oriented generally perpendicular to the longitudinal axis of the barrel member.

20. The plunger rod assembly of claim 18 wherein said front flange includes a distal surface thereon which forms a semicircularly-shaped contact member to contact said lip member as said plunger rod is moved distally through the barrel member.

21. The plunger rod assembly of claim 18 wherein the force of the seal between the barrel member and said distal rib member is in proportion to the force applied by said front flange of said plunger rod to said lip member.

22. The plunger rod assembly of claim 18 wherein the force of the seal between the barrel member and said proximal rib member is in proportion to the force applied by said front flange of said plunger rod to said rear wall.

* * * * *